(12) United States Patent
Kuester et al.

(10) Patent No.: US 10,031,075 B2
(45) Date of Patent: Jul. 24, 2018

(54) DEVICE AND METHOD FOR IDENTIFYING REFRIGERANTS

(75) Inventors: Gerhard Kuester, Cologne (DE); Werner Grosse Bley, Bonn (DE)

(73) Assignee: Inficon GmbH, Cologne (DE)

( * ) Notice: Subject to any disclaimer, the term of this patent is extended or adjusted under 35 U.S.C. 154(b) by 265 days.

(21) Appl. No.: 14/241,281

(22) PCT Filed: Aug. 24, 2012

(86) PCT No.: PCT/EP2012/066531
§ 371 (c)(1),
(2), (4) Date: Feb. 26, 2014

(87) PCT Pub. No.: WO2013/030121
PCT Pub. Date: Mar. 7, 2013

(65) Prior Publication Data
US 2014/0361173 A1    Dec. 11, 2014

(30) Foreign Application Priority Data

Aug. 27, 2011 (DE) .................. 10 2011 111 836

(51) Int. Cl.
| | |
|---|---|
| *G01J 5/02* | (2006.01) |
| *G01N 21/3504* | (2014.01) |
| *G01J 5/08* | (2006.01) |
| *G01N 21/27* | (2006.01) |
| *G01N 21/31* | (2006.01) |

(52) U.S. Cl.
CPC ........ *G01N 21/3504* (2013.01); *G01J 5/0862* (2013.01); *G01N 21/276* (2013.01); *G01N 21/314* (2013.01); *G01N 2021/317* (2013.01)

(58) Field of Classification Search
CPC .................. G01N 21/3504; G01N 21/276
USPC ........... 250/339.01, 339.06, 339.07, 339.09, 250/339.13, 341.1, 341.8
See application file for complete search history.

(56) References Cited

U.S. PATENT DOCUMENTS

| | | | |
|---|---|---|---|
| 3,811,776 A | 5/1974 | Blau, Jr. | |
| 5,610,398 A | 3/1997 | Anderson et al. | |
| 5,610,400 A * | 3/1997 | Weckstrom | ........ G01N 21/3504 |
| | | | 250/339.13 |
| 6,018,983 A | 2/2000 | Jones et al. | |

(Continued)

FOREIGN PATENT DOCUMENTS

| | | |
|---|---|---|
| CN | 1259206 A | 7/2000 |
| CN | 2597984 Y | 1/2004 |

(Continued)

*Primary Examiner* — David Porta
*Assistant Examiner* — Carolyn Igyarto
(74) *Attorney, Agent, or Firm* — The Webb Law Firm

(57) ABSTRACT

A device for identifying refrigerants includes a gas cell, which has a test gas inlet and a test gas outlet, an infrared source that radiates through the gas cell, and at least one sensor that detects the infrared radiation that passes through the gas cell. At least one wide-band filter is provided between the infrared source and the sensor. The passband of the at least one wide-band filter includes the absorption spectra of the refrigerants to be detected and does not include the absorption spectrum of hydrocarbons. The gas cell is connected to a cartridge, which contains the refrigerant to be detected in pure form as a reference gas.

5 Claims, 3 Drawing Sheets

(56) References Cited

U.S. PATENT DOCUMENTS

| | | |
|---|---|---|
| 6,791,088 B1 | 9/2004 | Williams, II et al. |
| 6,995,360 B2 | 2/2006 | Jones et al. |
| 7,022,993 B1 | 4/2006 | Williams, II et al. |
| 7,535,007 B1 | 5/2009 | Freeman et al. |
| 2004/0149912 A1 | 8/2004 | Nomura et al. |
| 2012/0261569 A1 | 10/2012 | Grosse Bley et al. |

FOREIGN PATENT DOCUMENTS

| | | |
|---|---|---|
| DE | 29505014 U1 | 8/1996 |
| DE | 69809948 T2 | 10/2003 |
| DE | 102006010100 A1 | 9/2007 |
| EP | 1398618 A2 | 3/2004 |
| EP | 1850112 A1 | 10/2007 |
| GB | 979850 A | 1/1965 |
| GB | 1401942 A | 8/1975 |
| JP | H02124448 A | 5/1990 |
| JP | 2004101416 A | 4/2004 |
| WO | 2011076459 A1 | 6/2011 |

\* cited by examiner

DEVICE AND METHOD FOR IDENTIFYING REFRIGERANTS

CROSS-REFERENCE TO RELATED APPLICATIONS

This application is the United States national phase of International Application No. PCT/EP2012/066531 filed Aug. 24, 2012, and claims priority to German Patent Application No. 10 2011 111 836.9 filed Aug. 27, 2011, the disclosures of which are hereby incorporated in their entirety by reference.

BACKGROUND OF THE INVENTION

Field of the Invention

The invention refers to a device and a method for identifying refrigerants.

Description of Related Art

Because of legal requirements, various refrigerants are banned from use. In the automobile industry, for instance, the refrigerant HFO-1234yf will be used in the future instead of the previous refrigerant R134a. When an air condition system will be repaired in the future, it has to be possible to detect, for example, contaminations of the refrigerant HFO-1234yf by other refrigerants, such as e.g. R134a, in motor vehicle air condition systems.

For the purpose of detecting refrigerants, their different infrared absorption is used. In this regard, a gas cell is filled with the refrigerant to be tested (test refrigerant) and is radiated with infrared radiation passing therethrough. A sensor on the opposite side receives the radiation, with different parts of radiation being absorbed to a higher degree than others, depending on the refrigerants present in the gas cell. The absorption spectrum measured is converted into measurable electric voltage by the infrared sensor.

With the known measuring methods using infrared absorption, changes in temperature or in atmospheric pressure, ageing or a contamination of the gas cell cause measuring inaccuracies. A long-term stability of the measuring results can be achieved only with considerable effort.

SUMMARY OF THE INVENTION

It is an object of the invention to provide an improved device and an improved method for identifying refrigerants.

The device of the invention comprises at least one wide-band filter in the beam path from the infrared source through the gas cell into the sensor. The passband of the wide-band filter comprises at least one absorption wavelength of the refrigerant to be detected and comprises no absorption wavelength of a hydrocarbon. The device further comprises a cartridge holding the refrigerant to be detected as a reference gas. The cartridge is connected with a gas inlet of the gas cell.

According to the method of the invention, first, a measurement of the absorption within the passband of the wide-band filter is made, with the gas cell filled with the reference refrigerant. Subsequently, a measurement of the absorption spectrum within the passband of the wide-band filter is made, using the refrigerant to be tested. Finally, the measured absorption values for the reference refrigerant and the measured absorption values for the test refrigerant are divided to obtain a quotient. The quotient allows a statement on the relative purity of the refrigerant under test as compared with the pure reference refrigerant.

Preferably, measurements are in addition also made using at least one narrow-band filter. In this regard, a narrow-band filter should be provided whose passband only comprises the absorption wavelengths of the pure refrigerant to be detected, i.e. of the reference refrigerant. Another narrow-band filter should be matched to the absorption wavelength of another refrigerant that contaminates the refrigerant to be detected. The refrigerant to be detected typically is HFO-1234 yf, whose absorption value is at about 7.4 µm, among others. The passband of the first narrowband filter could therefore be in the range from 7.2 µm to 7.6 µm. A typical other refrigerant that could contaminate HFO-1234 yf is the refrigerant R134 a having an absorption wavelength of approximately 7.69 µm, among others. If it is desired to exclusively detect R123 a, the passband of the second narrow-band filter should be in the range from 7.5 µm to 7.9 µm. For the detection of HFO-1234 yf, the passband of the wide-band filter should have a lower limiting frequency of preferably 8 µm and an upper limiting frequency of preferably 14 µm. In this case, the absorption wavelengths of hydrocarbons are not transmitted by the filter, since they are lower than 8 µm.

For the detection of the refrigerant, at least one wavelength outside the passband of the wide-band filter can then be measured. This is the wavelength of absorption of the other, undesired refrigerant (for example R134a at 7.69 µm and/or hydrocarbons at 3.38 µm). Besides the wide-band filter, there will preferably be used the narrow-band filter for the detection of hydrocarbons at 3.38 µm, the narrow-band filter for the detection of R134a at 7.69 µm and a third narrow-band filter for the exclusive detection of HFO-123yf at 7.3 µm. The measured values obtained when each of these filters is used, are compared before with measured values of different gas compositions obtained during a calibration process. In this context, the gas composition among those gas compositions used in the calibration is considered as detected that is closest to the measured values.

Preferably in the event that the absorption of at least one wavelength within the passband of the wide-band filter corresponds to a known contaminating refrigerant, the method for identifying a refrigerant provides that the absorption of at least one wavelength outside the filter passband is measured that corresponds exclusively to the contaminating refrigerant. Subsequently, a linear system of equations is set up, in which, for each filter, the total absorption in the passband thereof is equated to a linear combination of the respective individual line absorptions. In other words: the individual line absorptions, i.e. the absorptions that can be associated with a respective refrigerant, are each provided with a coefficient and are then added, with the sum of the individual line absorptions being equated to the total absorption in the respective filter wavelength passband. By solving the linear equation system, it is possible to subsequently calculate any unknown concentration of a refrigerant by solving the equation system for the relevant coefficient of interest.

Finally, it is conceivable as an alternative that each refrigerant is measured using a corresponding narrow-band filter having a suitable cut-off wavelength matched to the respective refrigerant.

BRIEF DESCRIPTION OF THE DRAWINGS

The following is a detailed description of embodiments of the invention with reference to the Figures. In the Figures.

DESCRIPTION OF THE INVENTION

Figure 1:
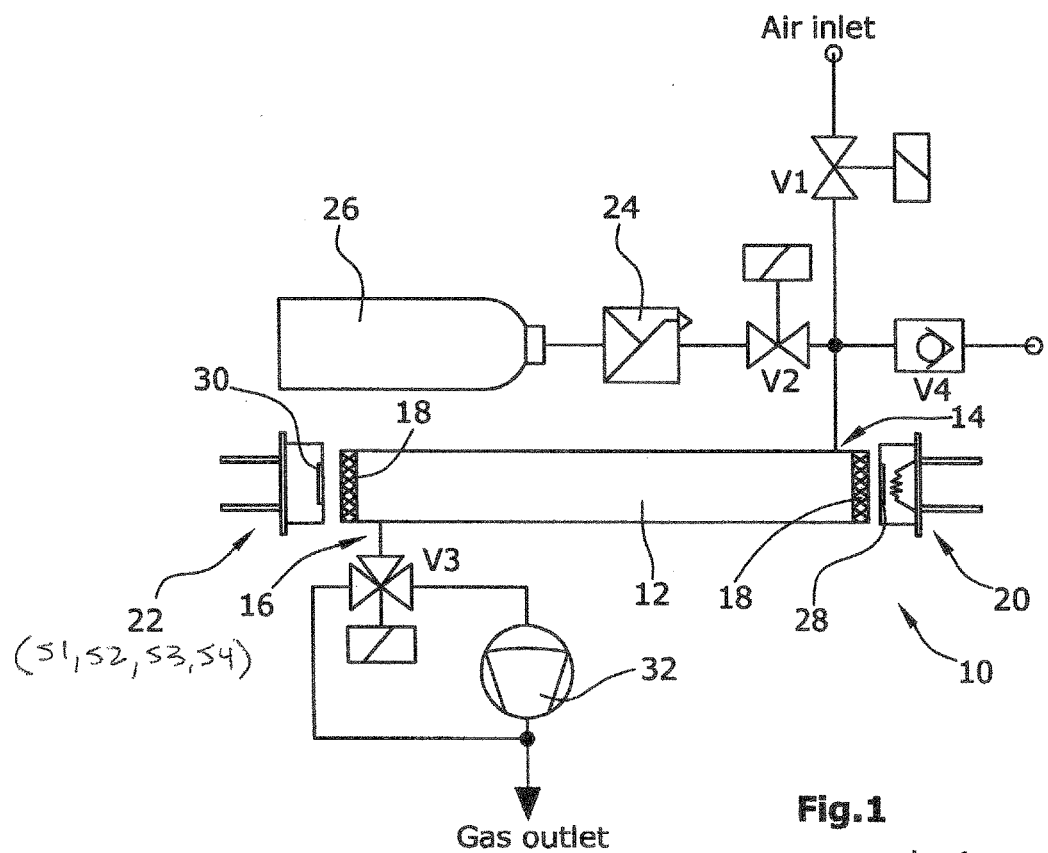
FIG. 1 shows an embodiment of the device of the present invention.

The device 10 of the present invention includes a gas cell 12 with a gas inlet 14 and a gas outlet 16. On two opposite sides, the gas cell is provided with CaF2 windows 18 that allow infrared radiation from an infrared source 20 to pass to a sensor 22 through the gas cell 12.

The gas inlet 14 of the gas cell 12 is connected with an air inlet via a controllable valve V1. A check valve V4 connects the gas inlet 14 with a test gas inlet for the refrigerant to be detected. A controllable valve V2 and a pressure reducer 24 connect the gas inlet 14 with a cartridge 26 that holds the refrigerant HFO-1234yf, which is to be detected, in pure form as a reference gas. The reference gas cartridge 26 is part of the device of the present invention.

Depending on the measurement, different optical filters 28, 30 are positioned in the beam path between the infrared source 20 and the sensor 22.

A controllable valve V3 and a membrane pump 32 connect the gas outlet 16 of the gas cell 12 with a gas outlet to atmosphere.

In each measurement, the refrigerant to be tested is compared with the reference refrigerant in the cartridge 26. Since all ambient conditions are identical both for the refrigerant to be tested and the reference refrigerant, they have no more relevance as disturbance variables.

The sensor 22 used includes four individual sensor elements, each having a respective infrared filter 30 arranged upstream thereof for the detection of a specific wavelength range. Thus, the four wavelength elements provide different output voltages for the gas mixture contained in the gas cell 12. The four voltages measured are compared with measured values for various gas compositions obtained before during a calibration process, wherein that calibrated gas composition is considered as detected that closest to the measured voltages.

Figure 4:
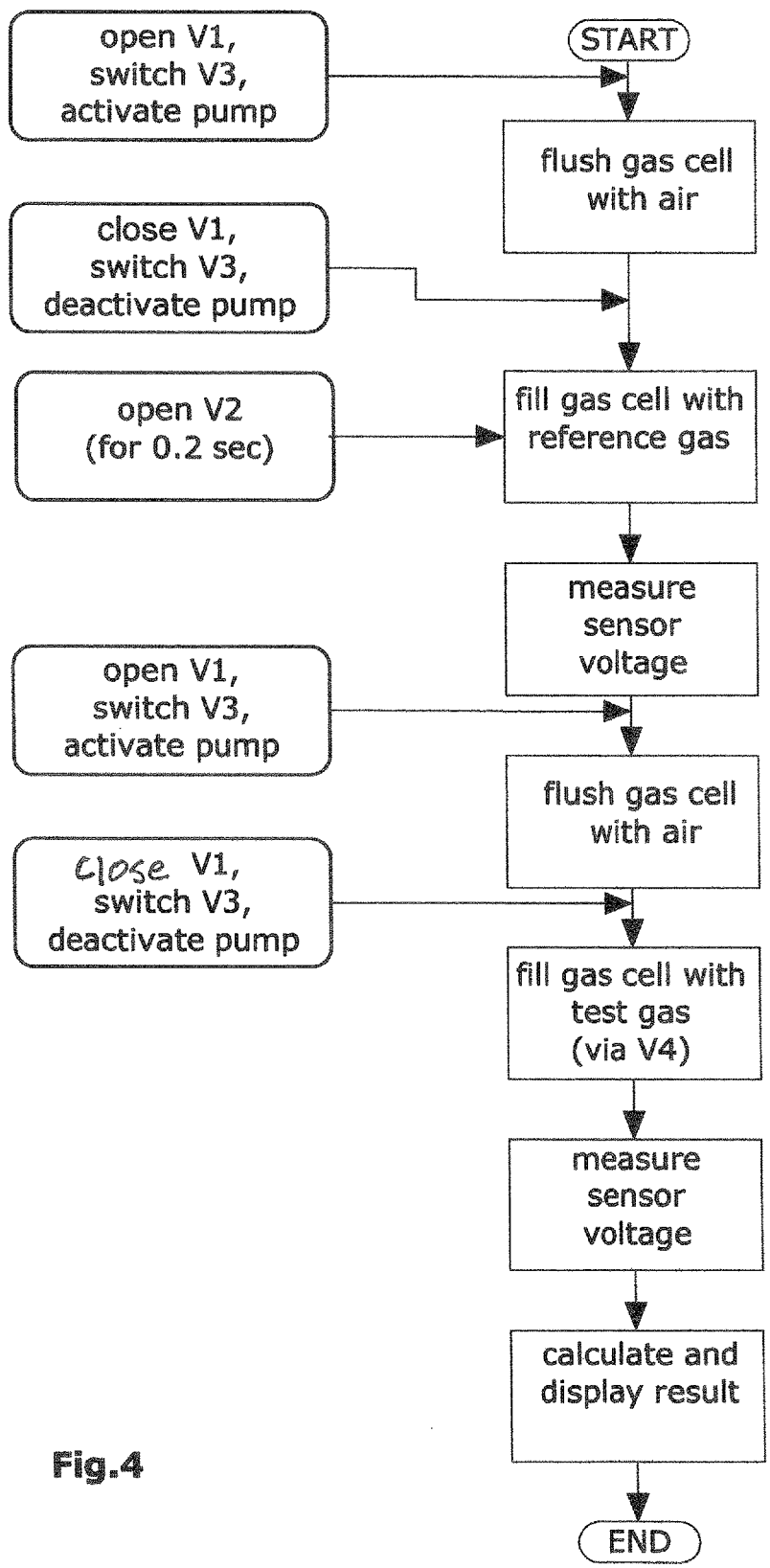
FIG. 4 shows a flow diagram of the method of the present invention.

FIG. 4 is a flow diagram showing the flow of the method of the invention implementing the device of FIG. 1. After the start, first, valve V1 is opened, then valve V3 is switched to the membrane pump 32 and the membrane pump 32 is activated. Thereby, the gas cell 12 is flushed with air from the air inlet.

Thereafter, valve V1 is closed to the air inlet and valve V3 is switched from the membrane pump 32 and the pump is deactivated. In order to fill the gas cell 12 with reference gas from the cartridge 26, valve V2 is opened for a period of 0.2 seconds. Thereafter, the voltages of the sensor elements of the senor 30 are measured.

Subsequently, valve V1 is opened, valve V3 is switched to the pump and the pump 32 is activated to flush the gas cell with air.

Thereafter, valve V1 is closed again, valve V3 is switched from the pump 32, the pump 32 is deactivated and the gas cell is filled with test gas via the check valve V4. After the gas cell 12 has been filled with test gas, the sensor voltages of the sensor 22 are measured and the proportion of the gas HFO-1234yf in the test gas is determined as described hereunder:

In a first variant, sensor elements S1, S2, S3 and S4 are used. The sensor element S1 has a wide-band filter with a passband of 8-14 µm associated therewith. The sensor element S2 is associated with a narrowband filter with a passband of 3.38 µm for hydrocarbons. The sensor element S3 is associated with a narrow-band filter with a passband of 7.69 µm for the refrigerant R134a. The sensor element S4 is associated with a narrow-band filter with a pass frequency of 7.3 µm for the refrigerant HFO-1234yf to be detected.

At the sensor element S1, with the gas cell 12 flooded with test gas, the voltage $V_{Meas,S1}$ is measured, and the reference voltage $V_{Ref,\,S1}$ is measured with the gas cell flooded with reference gas from the cartridge 26.

The result of a measurement is the quotient of $V_{Meas,S(i)}$ and $V_{Ref,S(i)}$:

$$a_{Meas} = \frac{V_{Meas,S1}}{V_{Ref,S1}},$$

$$b_{Meas} = \frac{V_{Meas,S2}}{V_{Ref,S2}},$$

$$c_{Meas} = \frac{V_{Meas,S3}}{V_{Ref,S3}},$$

$$d_{Meas} = \frac{V_{Meas,S4}}{V_{Ref,S4}}$$

$a_{Cal}$, $b_{Cal}$, $c_{Cal}$, $d_{Cal}$ → measured values of S1, S2, S3, S4, read from a file containing calibration values for specific gas mixtures The calibration values contained in the file are ratios $V_{Meas}/V_{Ref}$ for the four sensor elements S1, S2, S3 and S4 measured once during a calibration process.

An exemplary excerpt from a file containing calibration values reads as follows:

| | | | |
|---|---|---|---|
| 1.00000 | 1.00000 | 1.00000 | 1.00000 |
| 1.00231 | 1.00210 | 0.97337 | 1.00497 |
| 0.98800 | 1.00000 | 0.95000 | 1.00000 |
| 0.97600 | 0.99800 | 0.90800 | 1.00400 |

The first row (1,00000 1,00000 1,00000 1,00000) represents the voltage ratios for 100% pure HFO-1234yf. Since the measured signal voltages for the gas to be tested and for the referece gas (which is 100% pure HFO-1234yf) have the same values, the quotient of both is "1.000", respectively.

The second row shows the corresponding values for a mixture of 99.5% HFO-1234yf and 0.5% R134a, the third row shows the values for 99% HFO-1234yf and 1% R134a, etc.

For the determination of the purity of the HFO-1234yf refrigerant of the composition of the gas mixtures to be tested, the deviation between the absorptions measured and the absorptions to be expected for specific mixtures is determined using a metric according to the "least square method". In this manner, it is possible to determine which row of calibration data from the file shows the least deviation when compared with the measured values for the gas to be tested.

$$S = \left(\frac{a_{Cal}[i]}{b_{Cal}[i]} - \frac{a_{Meas}}{b_{Meas}}\right)^2 + \left(\frac{a_{Cal}[i]}{c_{Cal}[i]} - \frac{a_{Meas}}{c_{Meas}}\right)^2 +$$

$$\left(\frac{a_{Cal}[i]}{d_{Cal}[i]} - \frac{a_{Meas}}{d_{Meas}}\right)^2 + \ldots + (a_{Cal}[i] - a_{Meas})^2 +$$

-continued $$(b_{Cal}[i] - b_{Meas})^2 + (c_{Cal}[i] - c_{Meas})^2 + (d_{Cal}[i] - d_{Meas})^2$$

This calculation is made for all rows of the calibration file, wherein [i] in the above formula is the number of the row. The result is an array with as many values as there are rows in the calibration file. The smallest value in this array is the value of interest or the gas mixture it represents.

Figure 2:
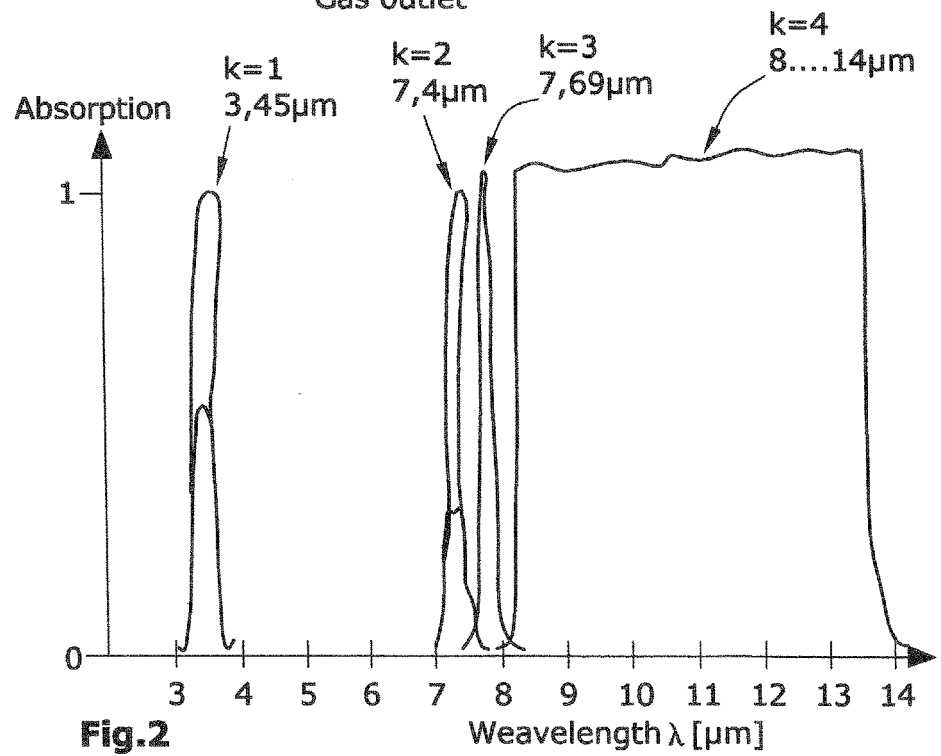
FIG. 2 illustrates the cut-off wavelength ranges of the filters used.

In an alternative embodiment of the measuring method of the invention the sensor 22 includes three infrared filters having different bandwidths. A first filter is matched to a wavelength of 7.4 µm for HFO-1234yf. Another filter is matched to a wavelength of 7.69 µm for R134a. A fourth filter is designed as a wide-band filter for the wavelength range from 8 to 14 µm for all possible refrigerants. Another narrow-band filter is matched to a wavelength of 3.45 µm for hydrocarbons. The passbands of these filters are illustrated in FIG. 2.

Measuring Principle:

For determining the concentrations of a refrigerant mixture of the gas components j, the absorption on the wavelengths k is measured, whereupon the linear equation system $$A_k = \sum_{j=1}^{AK} c_j \cdot a_{jk} \quad (1)$$

is solved, where the following designations apply:
$A_k$ total absorption of the gas mixture in the wavelength range k
$c_j$ concentration of the gas component j
$a_{jk}$ absorption of the component j in the wavelength range k
AK number of gas components Characteristic of the Solution:

One of the wavelength ranges is chosen with a width that includes all basically unknown refrigerants (8 . . . 14 µm) and as such allows for a statement on the purity without analyzing all spectral lines individually.

For this reason, no infrared photo-spectrometer is required, nor is it necessary to know all components contained in their entirety.

Measuring Process in Detail:

Calibration:
0. In preparation, each sensor is subjected to a factory calibration, wherein the factors $a_{jk}$ are determined individually (in compensation for filter tolerances). For this purpose, the substances j are respectively supplied (i.e. $c_j=1$) and the absorptions $a_{jk}$ are determined from equation (1).

Measurement:
1. The measurement starts with a zero determination by letting air into the cuvette. Thereby, all "zero absorptions" $A_{k,0}$ are determined.
2. The actual measurement is performed at a defined pressure (exactness of atmospheric pressure or measured with a pressure gage) after the unknown refrigerant mixture $A_k$ has been let in: all absorptions $A_k$ in the wavelength ranges k are measured.

Evaluation:
3. Using the known "zero absorption" $A_{k,0}$, the net absorptions $A_k = A_k - A_{k,0}$ are now calculated.
4. Using the net absorptions and the $a_{jk}$ known from the calibration, the equation system (1) can now be set up. The solution is obtained by known methods, e.g. by matrix inversion.
5. If more than one measurement is performed on the same mixture, it is possible, in a manner known per se, to perform an equalization calculation with the equation system which, in this case, is overdetermined (e.g. multiple linear regression) and to thereby also determine the standard deviation of the concentrations.

Figure 3:
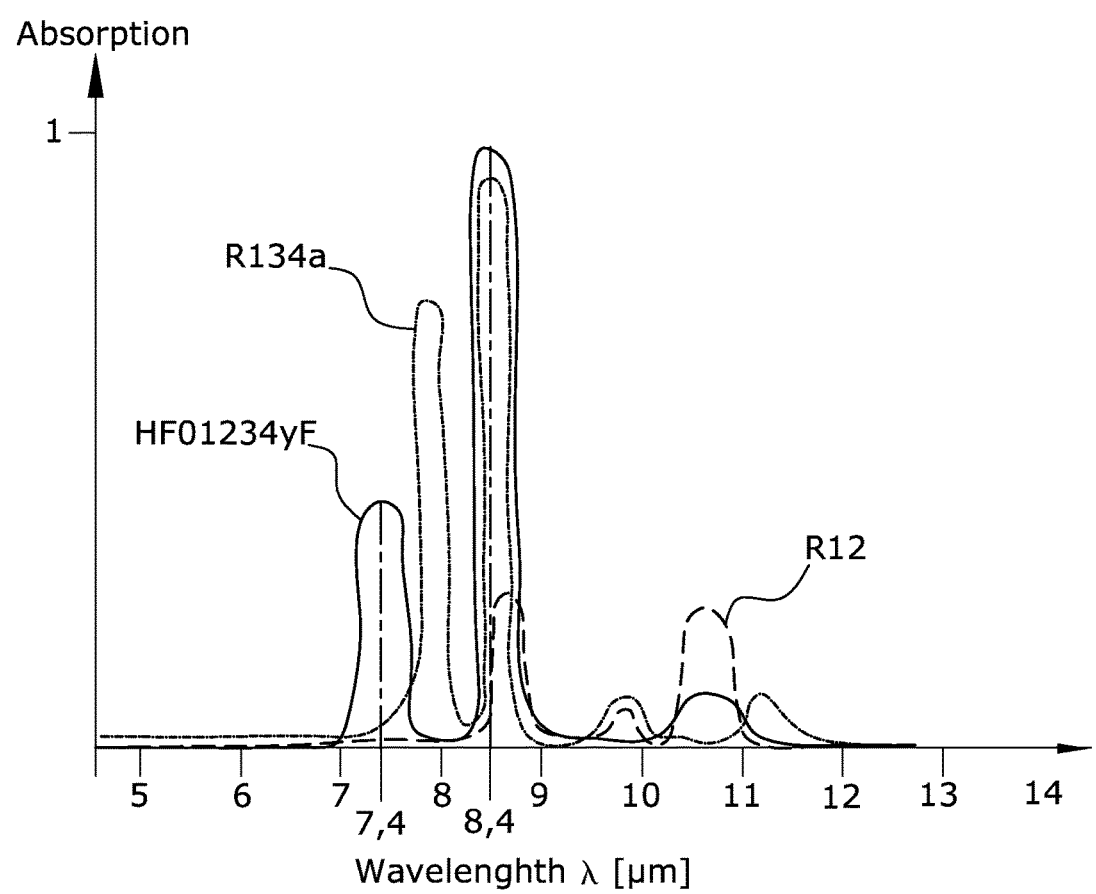
FIG. 3 shows the absorption spectra of a mixture of three refrigerants.

FIG. 3 illustrates typical absorption spectra of the refrigerants HFO-1234yf, R134a and r12.

a) reference value for sum of refrigerants

The wavelength range of 8 . . . 14 µm is representative of all conventional refrigerants, but excludes hydrocarbons, such as methane, propane, butane, . . . , $CO_2$ and water vapor. Thus, this is the ideal wavelength for representing the sum of all refrigerants and to form a 100% reference value for the necessary measurement of the purity of HFO-1234yf (this range is also used commercially for universal refrigerant detectors such as the INFICON devices D-TEKselect or HLD5000smart).

Accordingly, the absorption signal in this entire range is a measure of the sum of the partial pressures of all refrigerants.

b) measurand for the proportion of HFO-1234yf

Ideally, a free absorption line of HFO-1234yf would be sufficient to measure a signal for the partial pressure of HFO-1234yf alone. The HFO-1234yf line at 7.2 µm would be such a line, if it were not for the disturbing influence of water vapor absorption already occurring there.

For this reason, two lines have to be extracted for the determination of the HFO-1234yf partial pressure:
the line at 8.34 µm represents the sum of R134a and HFO-1234yf, and
the line at 7.69 µm represents R134a alone.

By subtracting the proportion of R134a known from the 7.69 µm line from the line at 8.43 µm, it is possible to determine the partial pressure of HFO-1234yf.

c) determination of the purity of HFO-1234yf and of the contamination by R134a

By forming a ratio between the HFO-1234yf partial pressure of b) and the total partial pressure of all refrigerants of a), a percentage for the purity of HFO-12343yf is obtained. Since, moreover, the partial pressure of R134a has been determined from the absorption at 7.69 µm, it is also possible to state whether the contamination is caused by R134a alone or by further (unknown) refrigerants.

The invention claimed is:
1. A method for identifying the purity of a gas under test, the method comprising:
radiating, by an infrared source, infrared radiation through a gas cell filled with a reference gas, wherein the gas cell is connected to a cartridge which contains the reference gas, wherein the reference gas comprises a 100 percent concentration of a first refrigerant,
measuring, by at least one sensor, infrared absorption of the reference gas in a passband of a filter, wherein the filter is provided between the infrared source and the sensor, the passband of the filter comprising an absorption spectrum of each of a plurality of refrigerants, and wherein the entire absorption spectrum of hydrocarbons is outside the passband of said filter,
radiating, by the infrared source, infrared radiation through the gas cell filled with the gas under test,
measuring, by the at least one sensor, infrared absorption of the gas under test in the passband of the filter,
dividing the measurement of the gas under test by the measurement of the reference gas to form a quotient of the measured values of the measurements on the reference gas and the gas under test, determining using the least square method a standard deviation between the quotient of the measured values of the measurements on the reference gas and the gas under test and a plurality of calibration values previously determined in a calibration process with gas compositions other than the gas under test, and determining a relative purity of the gas under test with respect to the reference gas based on the standard deviation between the quotient of the measured values and the plurality of calibration values.

2. The method of claim 1, further comprising:

measuring, by the at least one sensor, infrared absorption of the gas under test at at least one wavelength that is outside the passband of the filter, and comparing, using the least square method, the infrared absorption of the gas under test measured outside of the passband of the filter with wavelengths corresponding to values previously determined in the calibration process with gas compositions other than the gas under test.

3. The method of claim 1, the method further comprising:

determining proportions of an unknown refrigerant in the gas under test as coefficients of a linear equation system in which:

$$A_k = \sum_{j=1}^{AK} c_j a_{jk}$$

wherein, $A_k$ is a total absorption of the gas under test in a wavelength range k, $C_j$ is a concentration of an unknown contaminating refrigerant j, $a_{jk}$ is an absorption of the unknown contaminating refrigerant j in the wavelength range k, and AK is a number of unknown contaminating refrigerants.

4. The method of claim 1, further comprising:

measuring, by the at least one sensor, infrared absorption of a plurality of refrigerants to be detected in the gas under test, wherein for each refrigerant of the plurality of the refrigerants to be detected in the gas under test, the measurement is made using a respective narrow-band filter with a passband including the entire absorption wavelength of the respective refrigerant of the plurality of the refrigerants to be detected in the gas under test.

5. The method of claim 1, wherein the passband of the filter comprises wavelengths of more than 8 μm and less than 14 μm.

* * * * *